Figure 1:
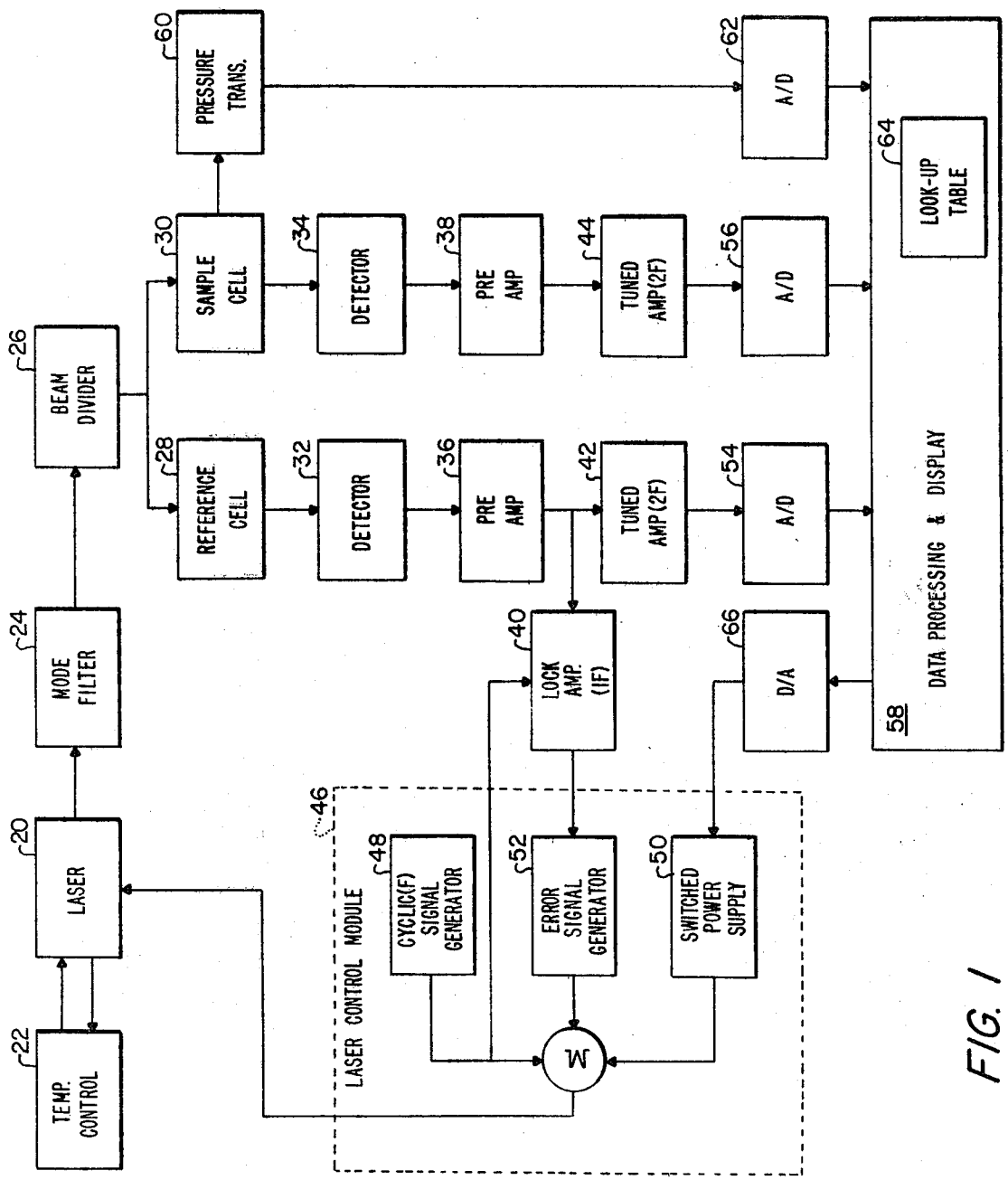

United States Patent [19]

Mantz et al.

[11] 4,410,273
[45] Oct. 18, 1983

[54] SCANNING LASER SPECTROMETER

[75] Inventors: Arlan W. Mantz, Acton; David L. Wall, Burlington; Dudley M. Chapman, Medford; Richard S. Eng, Newton; Kenneth W. Nill, Lexington, all of Mass.

[73] Assignee: Laser Analytics, Inc., Bedford, Mass.

[21] Appl. No.: 242,139

[22] Filed: Mar. 9, 1981

[51] Int. Cl.³ .......................... G01J 3/42; G01N 21/39
[52] U.S. Cl. ......................................... 356/319; 356/51; 250/339; 250/345; 250/354.1
[58] Field of Search .................... 356/51, 41, 319, 435; 250/339, 343, 345, 354.1

[56] References Cited

U.S. PATENT DOCUMENTS 3,805,074 4/1974 McCormack .................. 250/343 X
4,061,918 12/1977 Preier et al. ........................ 350/343

Primary Examiner—F. L. Evans
Attorney, Agent, or Firm—Schiller & Pandiscio

[57] ABSTRACT

A scanning spectrometer incorporating a scanning diode laser powered with a controllable injection current. The injection current control may be set at predetermined discrete levels. These levels may be varied in accordance with signals derived from a servo loop, and may have superimposed upon them a cyclically varying substantially constant amplitude current. The laser output is directed via a beam splitter to both sample and reference cells. The material in the reference cell is so selected as to provide absorption features at each of the desired frequencies. The cyclically varying current is provided with an amplitude sufficient to cause a frequency amplitude at least as great as the maximum breadth of each of these spectral features of interest. The preselected bias currents are selected so as to provide lasing action of the diode at or near each of the selected frequencies. A phase-locked amplifier tuned to the frequency of the cyclically varying current senses the position of the scanned laser output relative to that of the associated absorption feature and provides an error signal to adjust the bias current so as to center the cyclically scanned laser frequency on the selected absorption feature.

2 Claims, 4 Drawing Figures

SCANNING LASER SPECTROMETER

This invention relates to dual-beam spectrometric instruments, and more particularly to such instruments which employ a tunable laser to perform the spectral scan and make use of the reference beam for wavelength as well as intensity calibration.

Dual-beam spectrometers, which automatically compare the spectrum of a sample with that of a known reference material, are well known. In a common configuration, a broad-band light source is projected through a scanning monochrometer and the resulting narrow band radiation is divided, as by a beam splitter, half being passed through the sample and half through a reference standard. The narrow band radiation emergent from the sample is compared with that emergent from the reference sample. This may be accomplished, for instance, by providing separate photodetectors for the radiation passing through the sample and for that passing through the reference. The ratio of the signals from the two photodetectors is a measure of the ratio of the optical transmittance of the sample to that of the reference at the wavelength established by the monochrometer. Such measurements made at two or more wavelengths may be used to assay the sample with respect to the reference.

For a number of applications, a tunable laser may be substituted for the scanning monochrometer. Such systems are desirable, for instance, when extremely high resolution is desired at a limited number of wavelengths. A common configuration which has been used for this purpose makes use of semiconductor diode lasers. For such lasers, the output frequency is, among other things, current dependent. This dependence arises because the index of refraction of the semiconductor varies with the carrier concentration. Consequently, by varying the injection current in a known manner while otherwise stabilizing the laser, one may cause the laser to scan over a limited frequency range. As with a scanning monochrometer, the frequency calibration of such a device may be accomplished by observations of a known sample. Thus, the reference cell may serve not only as an absorbance (and therefore, concentration) standard, but as a wave length standard as well.

At extremely high resolution, very narrow spectral details must be used for wavelength standardization. A convenient method useful in the infrared makes use of the narrow absorption features produced by a gas sample at low pressure. If the laser output is passed through such a standard, the emergent radiation may be monitored to mark the instant the laser output corresponds to the frequency of the absorption feature. This signal may also be used in a servo loop to stabilize the laser frequency to the frequency of (or a limited frequency range about) the transmission minimum of the absorption feature.

It is often desirable to observe a limited range of frequencies about a number of discrete frequencies. A prior art method which has been used to accomplish this provides a tunable diode laser for each of the discrete frequencies. The outputs from the various lasers are then variously collected and divided and passed through both reference and sample. The reference cell is provided with a low pressure gas mixture selected so as to provide sharp absorption features at each of the desired frequencies. Each laser is caused to scan in frequency in the vicinity of the appropriate desired frequency. A detector and servo loop for each laser locks the center of the associated laser's scan to the corresponding frequency. While this approach has been used successfully, it will be appreciated that its realization is not without optical and electronic complexity.

At extremely high spectral resolution, the behaviour of absorption features becomes critically dependent on the environment. Line position, shape, and width are all affected, and the entire line must be observed to insure against spurious false absorbance readings. On the other hand, scanning an entire broad spectral range makes ineffecient use of the instrument, as well as being time consuming.

Accordingly, it is an object of the present invention to provide a high dispersion infrared scanning laser spectrometer which requires but a single laser and a single feedback loop for frequency stabilization, yet is capable of operation over two or more selected frequency ranges. Yet another object of the present invention is to provide such a spectrometer which may be rapidly and surely locked to the desired absorption features with assurance that the entire spectral feature of interest will be observed.

These and other objects are met in the present invention of a scanning spectrometer incorporating a scanning diode laser that is provided with a controllable injection current. The control means allows the injection current to be set at a predetermined levels, varied in accordance with signals derived from a servo loop, and further have a cyclically varying substantially constant amplitude current component. The laser output is directed via a beam splitter to both sample and reference cells. The material in the reference cell is selected to provide sharp, weakly absorbing features at each of the desired frequencies. Preferably, the spectral profile of these features approximately match one another and the anticipated spectral features of the sample. The preselected constant current components are so chosen as to produce lasing action of the diode at or near each of the selected frequencies. The cyclically varying current component is provided with an amplitude sufficient to cause a frequency shift of the laser output at least as great as the maximum breadth of the broadest spectral feature of interest. A phase-locked amplifier tuned to the frequency of the alternating current component senses the position of the cyclically scanned laser output relative to that of the associated absorption feature and provides an error signal to adjust the bias current so as to center the cyclically scanned laser frequency on the absorption feature.

The reference detector also supplies a signal to an amplifier tuned to twice the scan frequency. The rectified signal from this amplifier is proportional to the opacity of the absorption feature in the reference cell. A similar amplifier is provided for a detector viewing the optical signal transmitted through the sample cell. The outputs of these two amplifiers may be compared to derive the sample absorbance.

The use of a single scanning laser and a single servo loop which may be caused to lock the laser to a variety of selected frequencies will be seen to offer a number of advantages. Clearly, it is both optically and electronically less complex than a system which uses a separate laser and servo loop for each of the discrete frequencies. Further, it will be appreciated the arrangement provides great flexibility, in that by a mere substitution of reference cell and a change in injection current, the spectrometer may be reset for a differing set of frequencies. Indeed, in some cases substitution of reference cells may not be required.

Inasmuch as the laser is made to scan over a range of frequencies greater than the anticipated line widths, and as each scan is frequency locked to a similar reference sample, observation of the full line profile is assured.

Other objects of the invention will in part be obvious and will in part appear hereinafter. The invention accordingly comprises the apparatus possessing the construction, combination of elements, and arrangement of parts which are exemplified in the following detailed disclosure and the scope of the application of which will be indicated in the claims.

Figure 2A:
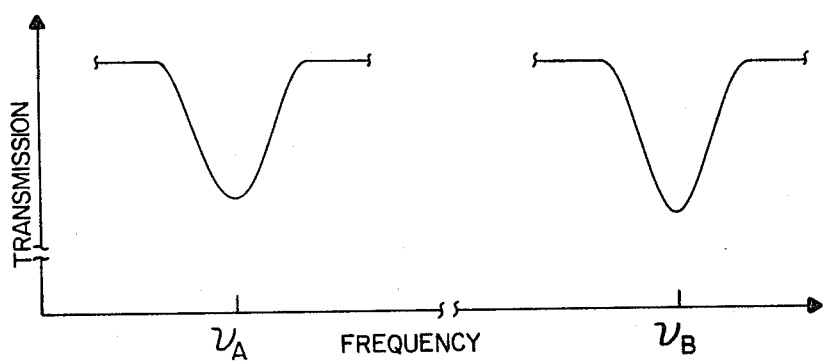

For a fuller understanding of the nature and objects of the present invention, reference should be had to the following detailed description taken in connection with the accompanying drawings wherein:

FIG. 1 is a schematic block diagram illustrating the relationship of essential components and the signal processing path therebetween in a preferred embodiment of the invention; and FIGS. 2(A-C) is a schematic representation of a portion of the absorption spectrum of a reference standard suitable for use in connection with the apparatus of FIG. 1, together with examples of representative waveforms as might appear at various locations within the signal path of FIG. 1.

It is to be understood that the graphs in FIG. 2 are diagramatic and no attempt has been made to indicate actual values of opacity, frequency, signal amplitude, or time on a linear or other scale.

Referring to FIG. 1, there may be seen a schematic block diagram of a scanning laser spectrometer made in accordance with the principles of the present invention. Laser 20 is a suitable tunable semiconductor diode laser. In a preferred embodiment, for use in the vicinity of 2300 cm$^{-1}$, laser 20 is a lead sulphide selenide (PbSSe) laser, although it will be understood that other semiconductor lasers, such as gallium arsenide (GaAs), other lead salts, and the like, could be used. It will be understood by those skilled in the art that laser 20 is mounted on the cold finger (not shown) of a suitable temperature controlled refrigerator. For the PbSSe laser chosen as an representative embodiment, stable operation requires the laser to be maintained in the vicinity of 30 degrees Kelvin with a thermal stability on the order of $0.3 \times 10^{-3}$ degrees Kelvin. To this end, the temperature of the laser/cold finger is monitored, and the refrigeration cycle of the temperature controlled refrigerator is appropriately varied, by means well known in the art, by a temperature stabilization feedback loop including a cryogenic temperature stabilizer 22.

The output of laser 20 is preferably passed through a mode selection filter 24. Typically, mode selection filter 24 may be a monochrometer with a pass band selected and adjusted to cover the spectral region of interest. The selected radiation from mode selection filter 24 is divided into a plurality of beams, as by beam divider 26, the beams being directed respectively through reference cell 28 and sample cell 30. Preferably, beam divider 26 is a beam splitter chosen to be spectrally neutral throughout the spectral region of interest and to divide the radiation equally between reference cell 28 and sample cell 30, although it will be understood that alternative means may be used and in some circumstance may be desirable.

Reference cell 28 and sample cell 30 are preferably partially evacuated long path optical sample cells of conventional design. In the embodiment chosen for illustrative purposes, cells 28 and 30 have widows of calcium fluoride and path lengths on the order of 10 centimeters. In this particular embodiment, the assay is for the ratio of $^{13}C$ to $^{12}C$ in $CO_2$, and reference cell 28 is filled with a gaseous mixture having a known percentage of carbon dioxide with a known isotopic ratio of carbon 13 to carbon 12 at a cell pressure of about 8 Torr (approximately 0.01 bar). While the carbon dioxide concentration and the isotopic abundance ratios are arbitrary, a typical mix might be 4 percent carbon dioxide and 1 percent carbon 13 to carbon 12. In this case, the sample to be assayed is preferably a similar concentration of carbon dioxide at a similar pressure. As will be described hereinafter, this assay utilizes the fine structure of the carbon dioxide band spectra arising from different branches of the $^{12}CO_2$ and $^{13}CO_2$ band spectra. Consequently, reference cell 28 and sample cell 30 should be closely matched in temperature throughut a measurement cycle. It will be understood that this may be accomplished by embedding both cells in a thermostated highly conductive mass (not shown).

Individual infrared detectors 32 and 34 are provided for each channel. Detectors 32 and 34 are electrical transducers producing electrical output signals proportional to the intensity of the infrared radiation incident upon them. The optical paths from beam divider 26 to detectors 32 and 34 are arranged to pass through reference cell 28 and sample cell 30, respectively, and all other radiation is preferably excluded. Thus, detectors 32 and 34 each ideally see a fixed proportion of the output of laser 20 attenuated respectively by the reference and the sample. As the laser is scanned, the attenuation varies, and consequently detectors 32 and 34 must be chosen not only on the basis of their spectral sensitivity but also so as to have response times compatible with the scanning frequency of the system and the fine structure of the absorption feature. In the particular embodiment under discussion, detectors 32 and 34 are lead selenide (PbSe) photoconductive detectors maintained at a temperature of about 240 degrees Kelvin by means (not shown) well known in the art.

The outputs of detectors 32 and 34 are preferably amplified to suitable levels by preamplifiers 36 and 38 respectively. The output of preamplifier 36 is supplied to amplifiers 40 and 42, while that of preamplifier 38 is supplied to amplifier 44. Amplifier 40 is phase-locked and tuned to the scanning frequency of laser 20 as will be described. Preferably, amplifiers 42 and 44 are also tuned amplifiers, in which case they are turned to twice this frequency. While not necessary, it is further desireable that 42 and 44 also be phase locked to the laser scan frequency.

The laser frequency stabilization loop is completed by laser control module 46. Laser control module 46 is the current supply for laser 20. For ease of exposition, laser control module 46 is shown as incorporating a cyclically varying current source 48, a switchable constant current source 50, and a variable error current source 52, connected such that the instantaneous sum of these three current components is the injection current of laser diode 20.

Cyclically varying current source 48 may be a sinusoidal, saw tooth, or similar signal generator. The amplitude of the cyclical variation is chosen, depending on the current-to-frequency response of the particular laser 20 and the maximum anticipated spectral width of the absorption features of interest, as will become apparent.

The frequency is chosen on the basis of laser intensity, detector response, and desired accuracy, as will be understood. In the particular embodiment being described, cyclically varying current source 48 provides a symmetrically increasing and decreasing current with a peak-to-peak amplitude on the order of a few tenths to a few milliamperes with a frequency below about two or three kHz.

Switchable current source 50 may be a stabilized power supply with switchable output taps provided at preselected values. The taps of switchable current source 50 are selected, on the basis of the separation of the spectral features of interest and the current-to-frequency response of the laser. Switchable power supply 50 in the example under discussion might provide laser 20 with nominal currents on the order of one ampere, tapped apart by a few to some tens of milliamperes. It will be understood that these currents might be adjusted for system alignment by some such device as trimming potentiometers (not shown). For reasons which will become apparent, it is desirable that the switching time of switchable current source 50 be short; risetimes corresponding to about 100 kHz are typical in systems of the type under discussion.

Error signal generator 52 produces a current which is proportional to the phase error of phase lock amplifier 40, as will be described. It will be understood that the amplitude range of this error signal delimits the capture range of the servo loop while the gain-bandwidth product of the loop delimits its time response. For the example under discussion the excursions of error signal generator 52 are typically on the order of a few to several milliamperes, and the gain-bandwidth product is typically on the order of 40 kiloHertz.

It will be appreciated that sources 48, 50, and 52 could be individual current sources as just described or alternatively could be realized by a single source passing through a controllable gain power amplifier.

In a preferred embodiment, the rectified outputs of amplifiers 42 and 44 are supplied respectively to analog to digital (A/D) converters 54 and 56. A/D converters 54 and 56 provide digital inputs to a data processing and display system 58. Data processing and display system 58 is provided to ratio and otherwise process the signals from A/D Converters 54 and 56 and further to provide an output display as, for instance, on a video terminal, as is well known in the art. Data processor and display system 58 is preferably a dedicated microcomputer with video and hard copy outputs, although it will be understood that the present invention could be realized otherwise. For instance, the outputs of amplifiers 42 and 44 could be displayed or ratioed by analog means, and the subsequent data reduction and control functions performed for instance by hand. A particular advantage of a data processing and display system 58 is, however, that the output signals from amplifiers 42 and 44 can be rapidly compared and accumulated until a predetermined signal-to-noise ratio is exceeded. When this condition has been determined, the data processing system 58 may be used to provide a signal which, when passed through a digital-to-analog converter 66 increments or decrements switchable current source 50, thereby initiating the measurement of the next spectral feature.

A further advantage of data processing display system 58 is that provision may be made for automatic calibration. For instance, while the content of reference cell 28 may be determined once and for all (if cell integrity can be assumed), the filling of sample cell 30 is subject to manipulative error. The determination of the absolute concentration of species of interest in sample cell 30 thus requires the determination of the pressure in the cell. The pressure in sample cell 30 may be determined by incorporating a pressure transducer 60. Pressure transducer 60 may, for instance, be a capacitance manometer. The output from pressure transducer 60 may be fed via an analog to digital converter 62 to data processing and display system 58 where it may be incorporated into calculations of absolute abundances. Additionally, instrumental constants, such as corrections for detector non-linearities, may be incorporated in a look up table 64 within the data processor.

The operation of the system depicted in the block diagram of FIG. 1 will now be described.

Referring to FIG. 2, at 2a there may be seen a schematic representation of a pair of absorption lines, denoted $\nu_A$ and $\nu_B$, as might be observed at high resolution by observing reference cell 28 (or sample cell 30) in transmission. For the illustrative example being discussed in detail, $\nu_A$ is the 2295.85 cm$^{-1}$ R(16) line of $^{13}C^{16}O_2$ while $\nu_B$ is the 2296.06 cm$^{-1}$ P(56) line of $^{12}C^{16}O_2$. This particular pair of lines was chosen for the example (a $^{13}C/^{12}C$ isotopic ratio detector) since the two lines have similar infrared absorbances despite a natural abundance ratio of about 100 to 1.

Figure 2B:
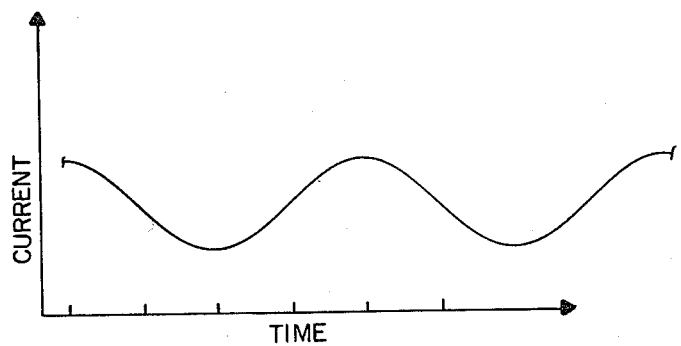
Figure 2C:
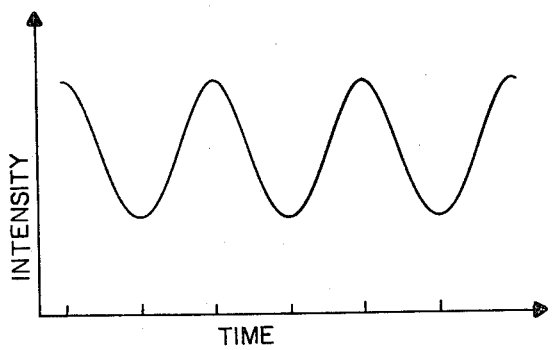

FIG. 2B is representative of the waveform from cyclic signal generator 48. As previously noted, the ascending and descending branches of this waveform are preferably of similar slope, the frequency of the waveform is preferably in the low audio range, and the amplitude is a few tenths milliampere. The exact value of the amplitude is chosen so as to produce an excursion of the laser diode frequency which is slightly greater than the line widths of the absorption profiles centered at $\nu_A$ and $\nu_B$. While the waveform is shown as sinusiodal, it will be understood that other waveforms may be employed. If the currents supplied by switchable power supply 50 and error signal generator 52 are adjusted such that the injection current they supply laser 20 is just less than that required to center the laser output frequency at $\nu_A$ by one-half the amplitude of this waveform, the summation of the output signals from signal generators 48, 50, and 52 (the output of laser control module 46) will then cause the laser to cyclically scan back and forth across the width of the absorption feature at $\nu_A$. In this circumstance, the laser energy passing through reference cell 28 and falling on detector 32 will, because of its cyclic variation in frequency, be cyclically attenuated as shown in FIG. 2C. The optical signal, and the electrical signal from detector 32 and preamp 36, will be modulated at twice the frequency of the cyclical scanning frequency, passing through one minimum (D) on the direct trace and a second minimum (R) on the retrace.

Amplifier 40, tuned and phase locked to the output of signal generator 48, is used as a phase sensitive detector to determine the lag or lead of waveform 2B compared to waveform 2C. This phase difference is in turn a direct measure of the frequency difference between the absorption maximum (transmission minimum) of the relevant absorption feature and the center frequency of the cyclical laser frequency scan. The phase difference signal from amplifier 40 serves as the input to error signal generator 52, which appropriately conditions (i.e., scales, and, if necessary, changes sign) so as to bias the current to laser 20, thereby locking the mid-frequency of the cyclical laser scan to the absorption maximum. With the mid-frequency of the laser scan centered on an absorption maximum and with the scan amplitude greater than the maximum line width of the absorption feature, the signal 2C fed by preamp 36 to amplifier 42 has an envelope which is proportional to the envelope of the absorption feature. While amplifier 42 may merely provide amplification, thereby providing an output waveform tracking this signal which may be later processed by means well known in the art, it is preferable that amplifier 42 be provided with a rectifier and time constant sufficient to integrate the signal, thereby providing a DC output which is proportional to the opacity of the absorption feature. It will be understood that if amplifier 42 is a tuned, phase-locked amplifier, the advantages of synchronous detection (i.e., noise and background supression) may be realized. If amplifier 42 further includes a log circuit, then the output will be proportional to absorbance. In any event, the output signal from amplifier 42 is processed by A/D converter 54 and made available as a digital signal within data processing and display system 58.

Inasmuch as the composition and pressure of the sample in sample cell 30 is similar to that in reference cell 28, detector 34 sees a signal which is similar to and synchronized with that at detector 32. That is, the frequency and phase relations between the waveform 2C caused by the interaction of cyclically scanned laser 20 and the gas mix in reference cell 28 will be mimicked by the interaction of the laser and the gas in sample cell 30. When the laser scan passing through reference cell 28 is locked to the R(16) $^{13}CO_2$ line of the gas in reference cell 28, the beam passing through sample cell 30 will be locked to the same line of the gas in sample cell 30. The signals at detector 32 and detector 34 will, however, generally differ in amplitude. Preamplifier 38 and amplifier 44 may be used, in like manner to preamplifier 36 and amplifier 42, to provide a DC signal proportional to the opacity or absorbance of the feature in sample cell 30. This signal is digitized by A/D converter 56 and also supplied to data system 58.

Because of differences between cell 28 and cell 30, detector 32 and detector 34, and amplifiers 36 and 38 and 42 and 44, the ratios of the signals in the reference channel and the sample channel is not directly the ratio of opacities in the two cells. By introducing identical samples into the two cells, or by interchanging cells, the proportionality factor between the two channels may be determined. This proportionality factor may also be entered in look-up table 64 in the data processing and display system. Similarly, non-linearities in detectors and amplifiers may be entered in the form of corrections in the look-up table. The ratio of the signal from A/D converter 56 to that from A/D converter 54, so calibrated, is a measure of the ratio of the partial pressures of the species giving rise to the absorption feature. For low concentrations of sample, as is the case under discussion, this ratio of corrected signals is very nearly linear with partial pressure ratios. Consequently, measurements of an unknown sample compared with a known reference provides a measure of the partial pressure, relative to the reference, of the sample. In the system described in detail, this results in relative partial pressures of the two isotopic forms of carbon dioxide. A measure of the pressure in the sample cell, as by a pressure transducer 60, yields data which may be processed together with the partial pressures to derive absolute isotopic abundances and concentration.

Switching between frequencies, as from 2295.85 cm$^{-1}$ to 2296.06 cm$^{-1}$ may be accomplished by incrementing the output from switched power supply 50. This may be accomlished either by computer command (as for instance when a measuring cycle on one line has been completed) or manually. In a system employing data processing and display unit 58, a particularly convenient way to accomplish this is to output digital commands corresponding to the gain of a power amplifier. That is, switched power supply 50 may be power amplifier having a variable gain, the gain signal being provided by data processing system 58 via D/A converter 56. As indicated hereinbefore, the rise time of any current transient intended to shift frequencies must either be faster than the tracking speed of the servo loop or the servo loop must be disabled during frequency shift.

It will be appreciated that the spectrometer system herein described possesses many unique advantages. For instance, the method of cyclically scanning a line and simultaneously locking to the center of the line of an absorption feature in the reference cell insures that the line opacity is accurately measured. Then again, the use of low pressure cells insures that measurements may be made relatively free from interferants. This last point may be of considerable importance in performing assays using the fine structure of infrared band spectra, as is done in the example described above, where considerable overlap of bands arising from different species may occur. Finally, it will be recognized that the switched power supply 50 need not be limited to a pair of values, and that the system is therefore readily expandable for use in multi-line analysis.

It will be recognized that various modifications can be made to the apparatus herein described. Thus, while for simplicity of exposition laser control module has been described as three separate current sources whose signals are summed, it may likewise be a stable power supply incorporating a variable gain power amplifier controlled by signals from an oscillator, an error detection circuit, and a multi-level switchable source. Indeed, all of these functions could be performed digitally. Further, it will be understood that the servo loop could utilize signals from the sample channel in addition to, or in place of, signals from the reference channel. Then too, multiple sample channels may be provided for simultaneous assay of a number of samples. Since these and other changes may be made in the above apparatus without departing from the scope of the invention herein involved, it is intended that all matter contained in the above description or shown in the accompanying drawings shall be interpreted in an illustrative and not a limiting sense.

What is claimed is:

1. A spectrometer system comprising in combination:
   a semiconductor diode laser capable of emitting energy at an output frequency variable in response to a varying injection current;
   temperature control means including means for maintaining said laser at a predetermined temperature;
   optical means including a beam divider for apportioning selected energy from said laser along a plurality of optical paths;
   first detection means disposed with respect to one of said paths for detecting said energy propagating along said one path;
   second detection means disposed with respect to another of said paths for detecting said energy propagating along said another path;
   means for disposing an absorbing reference material along said one path between said first detection means and said laser so as to attenuate a portion of said laser energy propagating along said one path, said reference material having selected absorption features of determinable spectral widths at optical frequencies of interest;

means for disposing a sample in said another optical path between said second detection means and said laser so as to intercept another portion of said laser energy propagating along said second path;

a plurality of amplifying means connected to said first and second detectors for providing electrical output signals proportional to the laser energy incident on the respective detectors;

laser control means for controlling said injection current of said laser, said laser control means including:
  (a) means for providing substantially constant currents at a plurality of predetermined values corresponding to injection currents suitable to cause said laser to emit said energy at discrete frequencies substantially corresponding to said selected absorption features,
  (b) means for cyclically varying said constant currents about said predetermined values by at least one predetermined amplitude at at least one predetermined frequency, said predetermined amplitude corresponding to a range of injection currents corresponding to a range of said output frequencies at least as large as a selected spectral width of one of said absorption features, and
  (c) means for varying said constant currents in response to an error signal, said amplifying means including phase detection means to determine the phase relationship between said means for cyclically varying and at least one said electrical output signal, said means for phase detection providing said error signal.

2. A spectrometer according to claim 1 and further including system control means including means for accumulating and comparing said electrical output signals responsively to one of said predetermined values of current so as to generate a sample-related value to a predetermined level of accuracy, and thereafter for commanding said laser control means to provide said substantially constant current at another of said preselected values.

* * * * *